United States Patent [19]

Haug et al.

[11] Patent Number: 5,117,038
[45] Date of Patent: May 26, 1992

[54] HERBICIDAL SUBSTITUTED PHENOXYPHENYLPROPIONIC ACID DERIVATIVES

[75] Inventors: Michael Haug, Bergisch Gladbach; Albrecht Marhold; Hans-Joachim Santel, both of Leverkusen; Klaus Lürssen; Robert R. Schmidt, both of Bergisch Gladbach, all of Fed. Rep. of Germany

[73] Assignee: Bayer Aktiengesellschaft, Leverkusen, Fed. Rep. of Germany

[21] Appl. No.: 482,134

[22] Filed: Feb. 16, 1990

[30] Foreign Application Priority Data

Feb. 23, 1989 [DE] Fed. Rep. of Germany ....... 3905518

[51] Int. Cl.$^5$ .............................................. C07C 69/76
[52] U.S. Cl. ...................... 560/55; 562/465; 562/840; 564/171; 71/107
[58] Field of Search ............... 560/55; 562/465, 840; 71/107

[56] References Cited

U.S. PATENT DOCUMENTS 4,377,713 3/1983 Keblys .................. 568/639
4,484,008 11/1984 Cook, Jr. et al. ............ 568/639

FOREIGN PATENT DOCUMENTS 0056119 7/1982 European Pat. Off. .
0075377 3/1983 European Pat. Off. .
0138183 4/1985 European Pat. Off. .
1941625 11/1970 Fed. Rep. of Germany .
3308374 10/1983 Fed. Rep. of Germany .

Primary Examiner—Paul J. Killos
Attorney, Agent, or Firm—Sprung Horn Kramer & Woods

[57] ABSTRACT

Herbicidal substituted phenoxyphenylpropionic acid derivatives of the formula $$\text{(I)}$$

in which
Q represents S, SO or $SO_2$,
m represents the numbers 0 or 1,
$R^1$ represents hydrogen, halogen, cyano or trifluoromethyl,
$R^2$ represents hydrogen or halogen,
$R^3$ represents halogen, cyano, trifluoromethyl, trifluoromethoxy or trifluoromethylsulphonyl,
$R^4$ represents hydrogen or halogen,
$R^5$ represents hydrogen or halogen,
$R^6$ represents hydrogen, cyano, carboxyl, alkyl optionally substituted by halogen or alkoxycarbonyl,
$R^7$ represents halogen, hydroxyl, amino, alkylamino, alkenylamino, alkynylamino, arylamino, aralkylamino, alkoxycarbonyl-alkylamino, cyanoamino, dialkylamino, dialkenylamino, alkylsulphonylamino, arylsulphonylamino, hydroxyamino, alkoxyamino, hydrazino, alkylsulphonylhydrazino, arylsulphonylhydrazino, alkylthio, arylthio, aralkylthio, alkoxycarbonylalkylthio or the grouping $O-R^8$.

5 Claims, No Drawings

HERBICIDAL SUBSTITUTED PHENOXYPHENYLPROPIONIC ACID DERIVATIVES

The invention relates to new substituted phenoxyphenylpropionic acid derivatives, a process and new intermediates for their preparation and their use as herbicides.

It has been disclosed that certain phenoxyphenyl compounds, such as, for example, methyl 3-(2,4-dichlorophenoxy)-6-nitro-benzoate (Bifenox) are active as herbicides (compare U.S. Pat. No. 3,652,645 and U.S. Pat. No. 3,776,715). However, the action of this known compound is not satisfactory in all matters.

New substituted phenoxyphenylpropionic acid derivatives of the general formula (I)

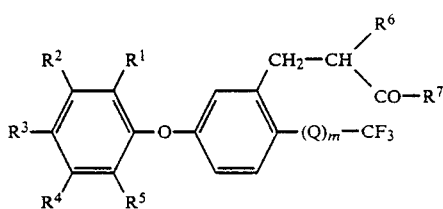

in which
- Q represents S, SO or $SO_2$,
- m represents the number 0 or 1,
- $R^1$ represents hydrogen, halogen, cyano or trifluoromethyl,
- $R^2$ represents hydrogen or halogen,
- $R^3$ represents halogen, cyano, trifluoromethyl, trifluoromethoxy or trifluoromethylsulphonyl,
- $R^4$ represents hydrogen or halogen,
- $R^5$ represents hydrogen or halogen,
- $R^6$ represents hydrogen, cyano, carboxyl, alkyl optionally substituted by halogen or alkoxycarbonyl,
- $R^7$ represents halogen, hydroxyl, amino, alkylamino, alkenylamino, alkynylamino, arylamino, aralkylamino, alkoxycarbonyl-alkylamino, cyanoamino, dialkylamino, dialkenylamino, alkylsulphonylamino, arylsulphonylamino, hydroxyamino, alkoxyamino, hydrazino, alkylsulphonylhydrazino, arylsulphonylhydrazino, alkylthio, arylthio, aralkylthio, alkoxycarbonylalkylthio or the grouping $O-R^8$, in which
  - $R^8$ represents a radical optionally substituted by halogen from the series comprising alkyl, alkenyl, alkynyl, alkoxyalkyl, alkylthioalkyl, alkylsulphinylalkyl, alkylsulphonylalkyl, aryloxyalkyl, trialkylsilylalkyl, arylthioalkyl, aralkoxyalkyl, aralkylthioalkyl, alkoxycarbonylalkyl, alkylaminocarbonylalkyl, aralkyl, azolylalkyl or an ammonium, alkylammonium, alkali metal or alkaline earth metal equivalent or the grouping

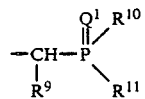

in which
- $R^9$ represents hydrogen, alkyl, aryl, furyl, thienyl or pyridyl,
- $R^{10}$ represents alkyl or alkoxy,
- $R^{11}$ represents alkoxy and
- $Q^1$ represents oxygen or sulphur, or
- $R^8$ represents the grouping $-(CH_2)_n-R^{12}$, in which
  - n represents the number 0, 1 or 2 and
  - $R^{12}$ represents a heterocyclic radical optionally substituted by halogen and/or alkyl, and from the series comprising furyl, tetrahydrofuryl, oxotetrahydrofuryl, thienyl, tetrahydrothienyl, perhydropyranyl, oxazolyl, perhydropyrrolyl, oxoperhydropyrrolyl, pyridinyl or pyrimidinyl, have now been found.

Halogen in each case denotes fluorine, chlorine, bromine or iodine The carbon chains in the individual radicals such as, for example, alkyl, alkenyl, alkoxy etc. are in each case straight-chain or branched.

It has further been found that the new substituted phenoxyphenylpropionic acid derivatives of the general formula (I) are obtained when (a) substituted phenoxybenzyl halides of the general formula (II)

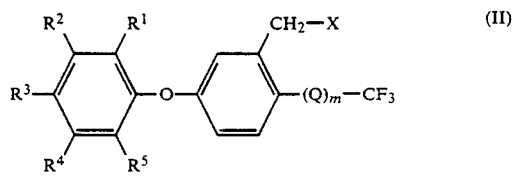

in which
- Q, $R^1$, $R^2$, $R^3$, $R^4$, $R^5$ and m have the abovementioned meanings and
- X represents halogen, are reacted with carbonyl compounds of the general formula (III)

$$R^6-CH_2-CO-R^7 \quad (III)$$

in which
- $R^6$ and $R^7$ have the abovementioned meanings, if appropriate in the presence of an acid acceptor and if appropriate in the presence of a diluent, or when (b) in the case in which in formula (I)
- $R^6$ represents carboxyl and
- $R^7$ represents hydroxyl and
- Q, $R^1$, $R^2$, $R^3$, $R^4$, $R^5$ and m have the abovementioned meanings, compounds of the general formula (I), in which
- $R^6$ represents alkoxycarbonyl and
- $R^7$ represents alkoxy and
- Q, $R^1$, $R^2$, $R^3$, $R^4$, $R^5$ and m have the abovementioned meanings, are reacted with water, if appropriate in the presence of a hydrolysis auxiliary and if appropriate in the presence of a diluent, or when (c) in the case in which in formula (I)
- $R^6$ represents hydrogen and
- $R^7$ represents hydroxyl and
- Q, $R^1$, $R^2$, $R^3$, $R^4$, $R^5$ and m have the abovementioned meanings, compounds of the general formula (I), in which
- $R^6$ represents carboxyl and
- $R^7$ represents hydroxyl and
- Q, $R^1$, $R^2$, $R^3$, $R^4$, R and m have the abovementioned meanings, are pyrolytically decarboxylated, or when (d) in the case in which in formula (I)
$R^6$ represents hydrogen and
$R^7$ represents halogen and
Q, $R^1$, $R^2$, $R^3$, $R^4$, $R^5$ and m have the abovementioned meanings,
compounds of the general formula (I), in which
$R^6$ represents hydrogen and
R represents hydroxyl and
Q, $R^1$, $R^2$, $R^3$, $R^4$, $R^5$ and m have the abovementioned meanings,
are reacted with a halogenating agent, if appropriate in the presence of a catalyst and if appropriate in the presence of an organic solvent, or when (e) in the case in which in formula (I)
$R^6$ represents hydrogen and
$R^7$, with the exception of halogen, has the abovementioned meaning and
Q, $R^1$, $R^2$, $R^3$, $R^4$, $R^5$ and m have the abovementioned meanings,
compounds of the general formula (I), in which
$R^6$ represents hydrogen and
$R^7$ represents halogen and
Q, $R^1$, $R^2$, $R^3$, $R^4$, $R^5$ and m have the abovementioned meanings,
are reacted with compounds of the formula (IV)

$$H-R^7 \qquad (IV)$$

in which
$R^7$, with the exception of halogen, has the abovementioned meaning,
if appropriate in the presence of an acid acceptor and if appropriate in the presence of a diluent, or when (f) in the case in which in formula (I)
$R^6$ represents hydrogen and
$R^7$ represents alkoxy and
Q, $R^1$, $R^2$, $R^3$, $R^4$, $R^5$ and m have the abovementioned meanings,
compounds of the general formula (I) in which
$R^6$ represents hydrogen and
$R^7$ represents hydroxyl and
Q, $R^1$, $R^2$, $R^3$, $R^4$, $R^5$ and m have the abovementioned meanings,
are reacted with alcohols of the formula (V)

$$HOR \qquad (V)$$

in which
R represents alkyl
if appropriate in the presence of a catalyst.

Finally, it has been found that the new substituted phenoxyphenylpropionic acid derivatives of the formula (I) exhibit outstanding herbicidal properties.

Surprisingly, the substituted phenoxyphenylpropionic acid derivatives of the formula (I) according to the invention are substantially more strongly active against weeds than methyl 3-(2,4-dichloro-phenoxy)-6-nitro-benzoate, which is a structurally similar previously known active compound with the same type of action.

The invention preferably relates to compounds of the formula (I) in which
Q represents S, SO or $SO_2$,
m represents the number 0 or 1,
$R^1$ represents hydrogen, halogen, cyano or trifluoromethyl,
$R^2$ represents hydrogen or halogen,
$R^3$ represents halogen, cyano, trifluoromethyl, trifluoromethoxy or trifluoromethylsulphonyl,
$R^4$ represents hydrogen or halogen,
$R^5$ represents hydrogen or halogen,
$R^6$ represents hydrogen, cyano, carboxyl, $C_1$–$C_4$-alkyl optionally substituted by fluorine and/or chlorine or $C_1$–$C_4$-alkoxy-carbonyl,
$R^7$ represents chlorine, hydroxyl, amino, $C_1$–$C_6$-alkylamino, $C_3$–$C_4$-alkenylamino, $C_3$–$C_4$-alkynylamino, phenylamino, benzylamino, $C_1$–$C_4$-alkoxy-carbonyl-$C_1$–$C_2$-alkylamino, cyanoamino, di-($C_1$–$C_4$-alkyl)-amino, di-($C_3$–$C_4$-alkenyl)-amino, $C_1$–$C_4$-alkylsulphonylamino, phenylsulphonylamino, tolylsulphonylamino, hydroxyamino, $C_1$–$C_6$-alkoxyamino, hydrazino, $C_1$–$C_4$-alkylsulphonylhydrazino, phenylsulphonylhydrazino, tolylsulphonylhyirazino, $C_1$–$C_4$-alkylthio, phenylthio, benzylthio, $C_1$–$C_4$-alkoxy-carbonyl-$C_1$–$C_2$-alkylthio or the grouping O—$R^8$, in which
$R^8$ represents a radical optionally substituted by fluorine and/or chlorine and from the series comprising $C_1$–$C_6$-alkyl, $C_3$–$C_4$-alkenyl, $C_3$–$C_4$-alkynyl, $C_1$–$C_4$-alkoxy-$C_1$–$C_4$-alkyl, $C_1$–$C_4$-alkylthio-$C_1$–$C_4$-alkyl, $C_1$–$C_4$-alkylsulphinyl-$C_1$–$C_4$-alkyl, $C_1$–$C_4$-alkylsulphonyl-$C_1$–$C_4$-alkyl, phenoxy-$C_1$–$C_3$-alkyl, trimethylsilylmethyl, phenylthio-$C_1$–$C_3$-alkyl, benzyloxy-$C_1$–$C_3$-alkyl, benzylthio-$C_1$–$C_3$-alkyl, $C_1$–$C_4$-alkoxy-carbonyl-$C_1$–$C_2$-alkyl, $C_1$–$C_4$-alkylamino-carbonyl-$C_1$–$C_2$-alkyl, benzyl, pyrazolyl-$C_1$–$C_4$-alkyl or an ammonium, a $C_1$–$C_4$-alkylammonium, or a sodium, potassium or calcium equivalent, or the grouping

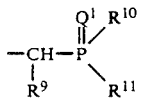

in which
$R^9$ represents hydrogen, $C_1$–$C_4$-alkyl, phenyl, furyl, thienyl or pyridyl,
$R^{10}$ represents $C_1$–$C_4$-alkyl or $C_1$–$C_4$-alkoxy,
$R^{11}$ represents $C_1$–$C_4$-alkoxy and
$Q^1$ represents oxygen or sulphur, or
$R^8$ represents the grouping —$(CH_2)_n$—$R^{12}$, in which
n represents the number 0, 1 or 2 and
$R^{12}$ represents a heterocyclic radical optionally substituted by fluorine, chlorine, bromine and/or $C_1$–$C_4$-alkyl and from the series comprising furyl, tetrahydrofuryl, oxotetrahydrofuryl, thienyl, tetrahydrothienyl, perhydropyranyl, oxazolyl, thiazolyl, thiadiazolyl, dioxolanyl, perhydropyrrolyl, oxoperhydropyrrolyl, pyridinyl or pyrimidinyl.

The invention in particular relates to compounds of the formula (I), in which
Q represents S or $SO_2$,
m represents the number 0 or 1,
$R^1$ represents hydrogen, fluorine or chlorine,
$R^2$ represents hydrogen, fluorine or chlorine,
$R^3$ represents trifluoromethyl or trifluoromethylsulphonyl,
$R^4$ represents hydrogen, fluorine or chlorine,
$R^5$ represents hydrogen, fluorine or chlorine, $R^6$ represents hydrogen, carboxyl or $C_1$-$C_3$-alkoxycarbonyl, $R^7$ represents chlorine, hydroxyl, amino, $C_1$-$C_4$-alkylamino, $C_1$-$C_4$-alkoxy-carbonyl-$C_1$-$C_2$-alkylamino, di-($C_1$-$C_3$-alkyl)-amino, $C_1$-$C_4$-alkylsulphonylamino, phenylsulphonylamino, hydroxyamino, cyanoamino, $C_1$-$C_4$-alkoxyamino, hydrazino, $C_1$-$C_4$-alkylsulphonylhydrazino, phenylsulphonylhydrazino, $C_1$-$C_4$-alkylthio or $C_1$-$C_4$-alkoxycarbonyl-$C_1$-$C_2$-alkylthio or the grouping O—$R^8$, in which $R^8$ represents $C_1$-$C_4$-alkyl, $C_1$-$C_2$-alkoxy-$C_1$-$C_2$-alkyl, $C_1$-$C_2$-alkylthio-$C_1$-$C_2$-alkyl, $C_1$-$C_2$-alkylsulphinyl-$C_1$-$C_2$-alkyl, $C_1$-$C_2$-alkylsulphonyl-$C_1$-$C_2$-alkyl, benzyloxy-$C_1$-$C_3$-alkyl, benzylthio-$C_1$-$C_3$-alkyl, $C_1$-$C_4$-alkoxycarbonyl-$C_1$-$C_2$-alkyl, $C_1$-$C_4$-alkylamino-carbonyl-$C_1$-$C_2$-alkyl, benzyl or an ammonium, a $C_1$-$C_3$-alkylammonium, or a sodium or potassium equivalent, or the grouping

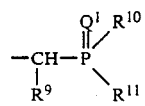

in which
$R^9$ represents hydrogen, methyl, phenyl, furyl, thienyl or pyridyl,
$R^{10}$ represents methoxy or ethoxy,
$R^{11}$ represents methoxy or ethoxy and
$Q^1$ represents oxygen or sulphur, or
$R^8$ represents the grouping —$(CH_2)_n$—$R^{12}$, in which n represents the number 0, 1 or 2 and
$R^{12}$ represents a heterocyclic radical optionally substituted by chlorine and/or methyl and from the series comprising furyl, tetrahydrofuryl, thienyl, perhydropyranyl, oxazolyl, thiazolyl and dioxolanyl.

The invention relates very particularly to compounds of the formula (I) in which Q, m, and $R^1$ to $R^6$ have the abovementioned preferred and particularly preferred meanings and $R^7$ represents chlorine, hydroxyl, methoxy, ethoxy, n- or iso-propoxy, or n-, iso-, sec- or tert butoxy.

Examples of the substituted phenoxyphenylpropionic acid derivatives of the formula (I) are shown in Table 1 below.

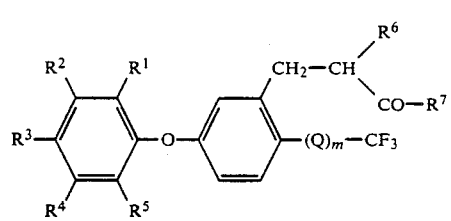

TABLE 1

| $R^1$ | $R^2$ | $R^3$ | $R^4$ | $R^5$ | $R^6$ | $R^7$ | Q | m |
|---|---|---|---|---|---|---|---|---|
| Cl | H | $CF_3$ | H | H | H | OH | — | 0 |
| Cl | H | $CF_3$ | H | H | H | OH | S | 1 |
| Cl | H | $CF_3$ | H | H | H | OH | $SO_2$ | 1 |
| Cl | H | $CF_3$ | H | H | H | Cl | — | 0 |
| Cl | H | $CF_3$ | H | H | H | Cl | S | 1 |
| Cl | H | $CF_3$ | H | H | H | $OCH_3$ | — | 0 |
| Cl | H | $CF_3$ | H | H | H | $OC_2H_5$ | — | 0 |

TABLE 1-continued

| $R^1$ | $R^2$ | $R^3$ | $R^4$ | $R^5$ | $R^6$ | $R^7$ | Q | m |
|---|---|---|---|---|---|---|---|---|
| Cl | H | $CF_3$ | H | H | COOH | OH | — | 0 |
| Cl | H | $CF_3$ | H | H | $COOCH_3$ | $OCH_3$ | — | 0 |
| Cl | H | $CF_3$ | H | H | $COOC_2H_5$ | $OC_2H_5$ | — | 0 |
| Cl | H | $CF_3$ | H | Cl | H | OH | — | 0 |
| Cl | H | $CF_3$ | H | Cl | H | OH | S | 1 |
| Cl | H | $CF_3$ | H | Cl | H | OH | $SO_2$ | 1 |
| Cl | H | $CF_3$ | H | Cl | H | $OCH_3$ | $SO_2$ | 1 |
| Cl | H | $CF_3$ | H | Cl | H | Cl | — | 0 |
| Cl | H | $CF_3$ | H | Cl | H | Cl | S | 1 |
| Cl | H | $CF_3$ | H | Cl | H | $OCH_3$ | — | 0 |
| Cl | H | $CF_3$ | H | Cl | H | $OC_2H_5$ | — | 0 |
| Cl | H | $CF_3$ | H | Cl | COOH | OH | — | 0 |
| Cl | H | $CF_3$ | H | Cl | $COOCH_3$ | $OCH_3$ | — | 0 |
| Cl | H | $CF_3$ | H | Cl | $COOC_2H_5$ | $OC_2H_5$ | — | 0 |
| Cl | H | $CF_3$ | H | F | H | OH | — | 0 |
| Cl | H | $CF_3$ | H | F | H | OH | S | 1 |
| Cl | H | $CF_3$ | H | F | H | OH | $SO_2$ | 1 |
| Cl | H | $CF_3$ | H | F | H | Cl | — | 0 |
| Cl | H | $CF_3$ | H | F | H | Cl | S | 1 |
| Cl | H | $CF_3$ | H | F | H | $OCH_3$ | — | 0 |
| Cl | H | $CF_3$ | H | F | H | $OC_2H_5$ | — | 0 |
| Cl | H | $CF_3$ | H | F | COOH | OH | — | 0 |
| Cl | H | $CF_3$ | H | F | $COOCH_3$ | $OCH_3$ | — | 0 |
| Cl | H | $CF_3$ | H | F | $COOC_2H_5$ | $OC_2H_5$ | — | 0 |
| Cl | H | $CF_3$ | F | F | H | OH | — | 0 |
| Cl | H | $CF_3$ | F | F | H | $OCH_3$ | — | 0 |
| Cl | H | $CF_3$ | F | F | H | $OC_2H_5$ | — | 0 |
| Cl | H | $CF_3$ | F | F | COOH | OH | — | 0 |
| Cl | H | $CF_3$ | H | Cl | H | $OC_2H_5$ | $SO_2$ | 1 |
| Cl | H | $CF_3$ | F | F | $COOCH_3$ | $OCH_3$ | — | 0 |
| Cl | H | $CF_3$ | F | F | $COOCH_3$ | $OCH_3$ | S | 1 |
| Cl | H | $CF_3$ | Cl | Cl | H | OH | — | 0 |
| Cl | H | $CF_3$ | Cl | Cl | H | Cl | — | 0 |
| Cl | H | $CF_3$ | Cl | Cl | H | $OCH_3$ | — | 0 |
| Cl | H | $CF_3$ | Cl | Cl | H | $OC_2H_5$ | — | 0 |
| Cl | H | $CF_3$ | Cl | Cl | H | OH | S | 1 |
| Cl | H | $CF_3$ | Cl | Cl | H | OH | $SO_2$ | 1 |
| Cl | H | $CF_3$ | Cl | Cl | COOH | OH | — | 0 |
| Cl | H | $CF_3$ | Cl | Cl | $COOH_3$ | $OCH_3$ | — | 0 |
| Cl | H | $CF_3$ | Cl | Cl | $COOC_2H_5$ | $OC_2H_5$ | — | 0 |
| Cl | H | $CF_3$ | Cl | Cl | $COOC_2H_5$ | $OC_2H_5$ | S | 1 |
| Cl | H | $CF_3$ | F | Cl | H | OH | — | 0 |
| Cl | H | $CF_3$ | F | Cl | H | Cl | — | 0 |
| Cl | H | $CF_3$ | F | Cl | H | OH | S | 1 |
| Cl | H | $CF_3$ | F | Cl | H | OH | $SO_2$ | 1 |
| Cl | H | $CF_3$ | F | Cl | H | $OCH_3$ | — | 0 |
| Cl | H | $CF_3$ | F | Cl | H | $OC_2H_5$ | — | 0 |
| Cl | H | $CF_3$ | F | Cl | COOH | OH | — | 0 |
| Cl | H | $CF_3$ | F | Cl | $COOCH_3$ | $OCH_3$ | — | 0 |
| Cl | H | $CF_3$ | F | Cl | $COOC_2H_5$ | $OC_2H_5$ | — | 0 |
| Cl | H | $CF_3$ | H | F | H | $OCH_3$ | $SO_2$ | 1 |
| Cl | H | $CF_3$ | H | Cl | H | $OC_3H_7$ | — | 0 |
| Cl | H | $CF_3$ | H | Cl | H | $OCH(CH_3)_2$ | — | 0 |
| Cl | H | $CF_3$ | H | Cl | H | $OC_4H_9$ | — | 0 |
| Cl | H | $CF_3$ | H | Cl | H | $OCH_2CH(CH_3)_2$ | — | 0 |
| Cl | H | $CF_3$ | H | Cl | H | $OCH_2COOCH_3$ | — | 0 |
| Cl | H | $CF_3$ | H | Cl | H | $SCH_2COOCH_3$ | — | 0 |
| Cl | H | $CF_3$ | H | Cl | H | $OCH_2CH_2OCH_3$ | — | 0 |
| Cl | H | $CF_3$ | H | Cl | H | $OCH_2CH_2SC_2H_5$ | — | 0 |
| Cl | H | $CF_3$ | H | Cl | H | $SC_2H_5$ | — | 0 |
| Cl | H | $CF_3$ | H | Cl | H | $SC_4H_9$ | — | 0 |
| Cl | H | $CF_3$ | H | Cl | H | $OCH_2P(OC_2H_5)_2$ (with =O) | — | 0 |
| Cl | H | $CF_3$ | H | Cl | H | $NHCH(CH_3)_2$ | — | 0 |
| Cl | H | $CF_3$ | H | Cl | H | $N(CH_3)_2$ | — | 0 |
| Cl | H | $CF_3$ | H | Cl | H | $NHSO_2CH_3$ | — | 0 |
| Cl | H | $CF_3$ | H | Cl | H | $NHOC_2H_5$ | — | 0 |
| Cl | H | $CF_3$ | H | Cl | H | $NHCH_2COOC_2H_5$ | — | 0 |
| Cl | H | $CF_3$ | H | Cl | H | $OCH_2$-(furyl) | — | 0 |

TABLE 1-continued

Examples of the compounds of the formula (I)

| R¹ | R² | R³ | R⁴ | R⁵ | R⁶ | R⁷ | Q | m |
|----|----|----|----|----|----|----|----|----|
| Cl | H | CF₃ | H | Cl | H | OCH₂—(tetrahydropyran-2-yl) | — | 0 |
| Cl | H | CF₃ | H | F | H | OC₂H₅ | SO₂ | 1 |

If, for example 2-trifluoromethyl-5-(2-chloro-4-trifluoromethyl-phenoxy)-benzyl chloride and diethyl malonate are used as starting substances for process (a) according to the invention, the course of the reaction can be represented by the following equation:

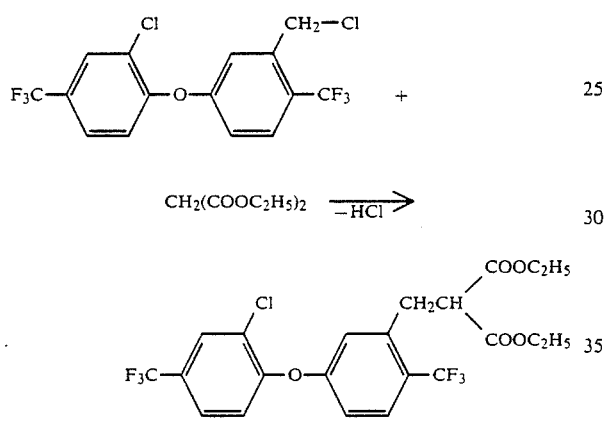

If, for example, bis methyl α-[2-trifluoromethylthio-5-(2-chloro-6-fluoro-4-trifluoromethylphenoxy)-benzyl]-malonate is used as a starting substance for process (b) according to the invention, the course of the reaction can be represented by the following equation:

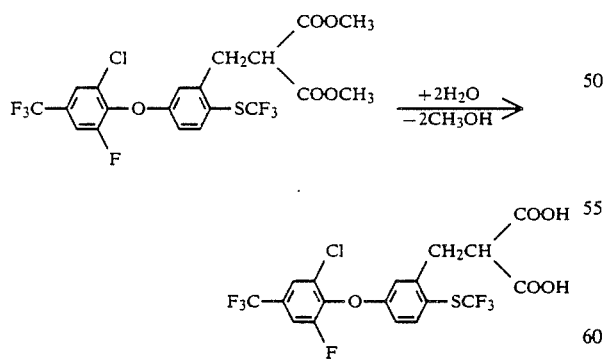

If, for example, α-[2-trifluoromethyl-5-(2,3,6-trichloro-4-trifluoromethyl-phenoxy)-benzyl]-malonic acid is used as a starting substance for process (c) according to the invention, the course of the reaction can be outlined by the following equation:

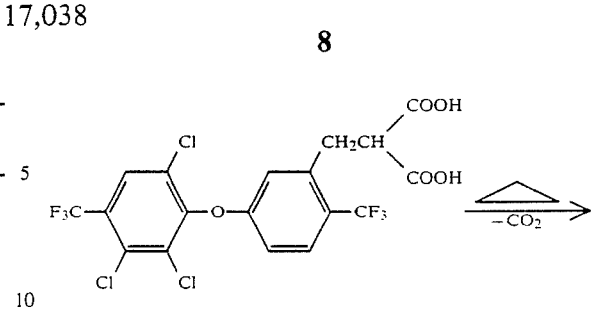

If, for example, β-[2-trifluoromethylsulphonyl-5-(2,6-dichloro-4-trifluoromethyl-phenoxy)-phenyl]-propionic acid and thionyl chloride are used as starting substances for process (d) according to the invention, the course of the reaction can be outlined by the following equation:

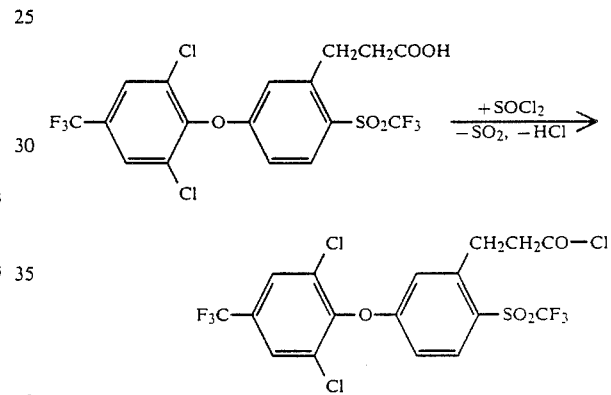

If, for example, β-[2-trifluoromethylthio-5-(2,3,6-trifluoro-4-trifluoromethyl-phenoxy)-phenyl]-propionyl chloride and methyl mercaptoacetate are used as starting substances for process (e) according to the invention, the course of the reaction can be outlined by the following equation:

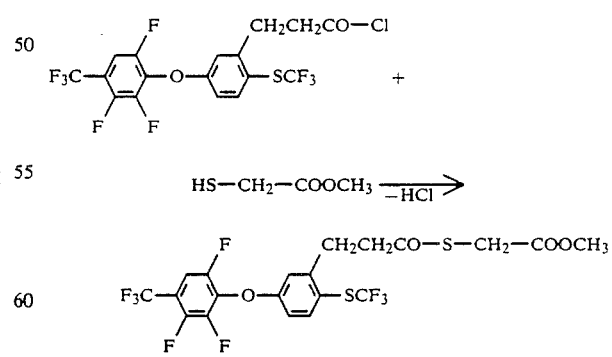

If, for example, β-[2-trifluoromethyl-5-(2,6-dichloro-3-fluoro-4-trifluoromethyl-phenoxy)-phenyl]-propionic acid and butanol are used as starting substances for process (f) according to the invention, the course of the reaction can be outlined by the following equation:

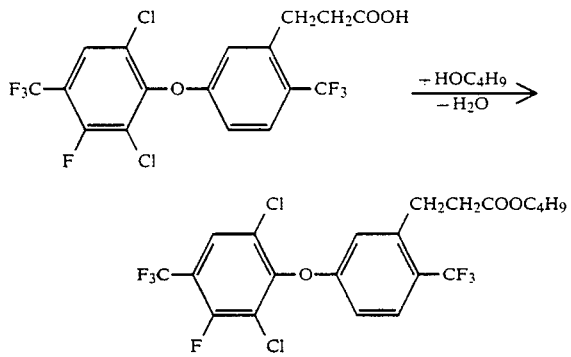

Formula (II) provides a general definition of the substituted phenoxybenzyl halides to be used as starting substances for the preparation of compounds of the formula (I) in process (a) according to the invention.

In formula (II), Q, $R^1$, $R^2$, $R^3$, $R^4$, $R^5$ and m preferably or in particular have those meanings which have already been indicated above as preferred or as particularly preferred for Q, $R^1$, $R^2$, $R^3$, $R^4$, $R^5$ and m in connection with the description of the compounds of the formula (I) according to the invention and X preferably represents chlorine or bromine.

Examples of the starting substances of the formula (II) are shown in Table 2 below.

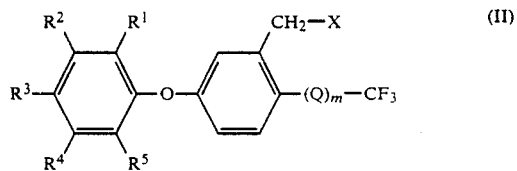

TABLE 2

| $R^1$ | $R^2$ | $R^3$ | $R^4$ | $R^5$ | Q | m | X |
|---|---|---|---|---|---|---|---|
| Cl | H | $CF_3$ | H | H | — | 0 | Cl |
| Cl | H | $CF_3$ | H | H | — | 0 | Br |
| Cl | H | $CF_3$ | H | H | S | 1 | Br |
| Cl | H | $CF_3$ | H | H | $SO_2$ | 1 | Cl |
| Cl | H | $CF_3$ | H | Cl | — | 0 | Cl |
| Cl | H | $CF_3$ | H | Cl | — | 0 | Br |
| Cl | H | $CF_3$ | H | Cl | S | 1 | Br |
| Cl | H | $CF_3$ | H | Cl | $SO_2$ | 1 | Cl |
| Cl | H | $CF_3$ | H | Cl | — | 0 | Cl |
| Cl | H | $CF_3$ | H | F | — | 0 | Br |
| Cl | H | $CF_3$ | H | F | S | 1 | Br |
| Cl | H | $CF_3$ | H | F | $SO_2$ | 1 | Cl |
| Cl | H | $CF_3$ | F | F | — | 0 | Cl |
| Cl | H | $CF_3$ | F | F | — | 0 | Br |
| Cl | H | $CF_3$ | F | F | S | 1 | Br |
| Cl | H | $CF_3$ | F | F | $SO_2$ | 1 | Cl |
| Cl | H | $CF_3$ | Cl | Cl | — | 0 | Cl |
| Cl | H | $CF_3$ | Cl | Cl | — | 0 | Br |
| Cl | H | $CF_3$ | Cl | Cl | S | 1 | Br |
| Cl | H | $CF_3$ | Cl | Cl | $SO_2$ | 1 | Cl |
| Cl | H | $CF_3$ | F | Cl | — | 0 | Cl |
| Cl | H | $CF_3$ | F | Cl | — | 0 | Br |
| Cl | H | $CF_3$ | F | Cl | S | 1 | Br |
| Cl | H | $CF_3$ | F | Cl | $SO_2$ | 1 | Cl |
| Cl | H | $SO_2CF_3$ | H | H | — | 0 | Br |
| Cl | H | $SO_2CF_3$ | H | Cl | — | 0 | Br |
| Cl | H | $CF_3$ | H | Cl | $SO_2$ | 1 | Br |

The starting substances of the formula (II) were previously unknown from the literature. The new substituted phenoxybenzyl halides of the formula (II) are obtained when substituted phenoxytoluenes of the general formula (VI)

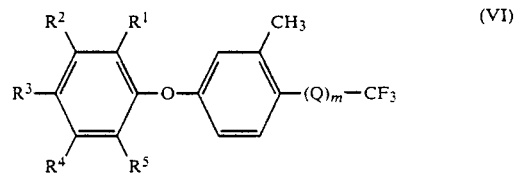

in which

Q, $R^1$, $R^2$, $R^3$, $R^4$, $R^5$ and m have the abovementioned meanings, are reacted with halogenating agents, such as, for example, chlorine, bromine, sulphuryl chloride, N-chloro- or N-bromo-succinimide, if appropriate under irradiation, for example using mercury immersion lamps, if appropriate in the presence of catalysts, such as, for example, benzoyl peroxide or azo-bis-isobutyronitrile, and if appropriate in the presence of diluents, such as, for example, tetrachloromethane, at temperatures between 20° C. and 150° C.

Formula (VI) provides a general definition of the substituted phenoxytoluenes required as intermediates. In formula (VI), Q, $R^1$, $R^2$, $R^3$, $R^4$, $R^5$ and m preferably or in particular have those meanings which have already been indicated as preferred or as particularly preferred for Q, $R^1$, $R^2$, $R^3$, $R^4$, $R^5$ and m in connection with the description of the compounds of the formula (I) according to the invention.

Examples of the intermediates of the formula (VI) are shown in Table 3 below.

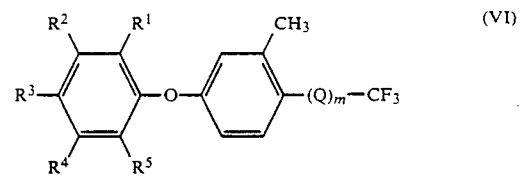

TABLE 3

| $R^1$ | $R^2$ | $R^3$ | $R^4$ | $R^5$ | Q | m |
|---|---|---|---|---|---|---|
| Cl | H | $CF_3$ | H | H | — | 0 |
| Cl | H | $CF_3$ | H | H | S | 1 |
| Cl | H | $CF_3$ | H | H | $SO_2$ | 1 |
| Cl | H | $CF_3$ | H | Cl | — | 0 |
| Cl | H | $CF_3$ | H | Cl | S | 1 |
| Cl | H | $CF_3$ | H | Cl | $SO_2$ | 1 |
| Cl | H | $CF_3$ | H | F | — | 0 |
| Cl | H | $CF_3$ | H | F | S | 1 |
| Cl | H | $CF_3$ | H | F | $SO_2$ | 1 |
| Cl | H | $CF_3$ | F | F | — | 0 |
| Cl | H | $CF_3$ | F | F | S | 1 |
| Cl | H | $CF_3$ | F | F | $SO_2$ | 1 |
| Cl | H | $CF_3$ | Cl | Cl | — | 0 |
| Cl | H | $CF_3$ | Cl | Cl | S | 1 |
| Cl | H | $CF_3$ | Cl | Cl | $SO_2$ | 1 |
| Cl | H | $CF_3$ | F | Cl | — | 0 |
| Cl | H | $CF_3$ | F | Cl | S | 1 |
| Cl | H | $CF_3$ | F | Cl | $SO_2$ | 1 |
| Cl | H | $SO_2CF_3$ | H | H | — | 0 |
| Cl | H | $SO_2CF_3$ | H | Cl | — | 0 |

The intermediates of the formula (VI) were previously unknown from the literature. The new substituted phenoxytoluenes of the formula (VI) are obtained when corresponding halogen-benzene derivatives of the general formula (VII)

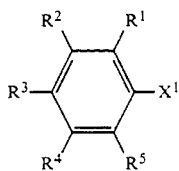
(VII)

in which
R¹, R², R³, R⁴ and R⁵ have the abovementioned meanings and
X¹ represents fluorine or chlorine,
are reacted with phenol derivatives of the general formula (VIII)

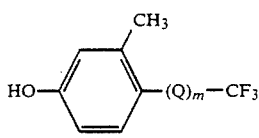
(VIII)

in which
Q and m have the abovementioned meanings,
in the presence of an acid acceptor, such as, for example, sodium hydroxide or potassium hydroxide, and in the presence of a diluent, such as, for example, dimethyl sulphoxide, at temperatures between 20° C. and 150° C. and the product is worked up by customary methods.

Formula (VII) provides the general definition of the halogenobenzene derivatives to be used as intermediates. In formula (VII), R¹, R², R³, R⁴ and R⁵ preferably or in particular have those meanings which have already been indicated as preferred or particularly preferred for R¹, R², R³, R⁴ and R⁵ in connection with the description of the compounds of the formula (I) according to the invention and X¹ preferably represents chlorine or fluorine.

Examples of the intermediates of the formula (VII) which may be mentioned are: 3,4-dichloro-benzotrifluoride, 3,4,5-trichloro-benzotrifluoride, 3,4-dichloro-5-fluoro-benzotrifluoride, 2,3,4,5-tetrachloro-benzotrifluoride, 3,5-dichloro-2,4-difluoro-benzotrifluoride and 3-chloro-4,5-difluorobenzotrifluoride.

The compounds of the formula (VII) are known and/or can be prepared by methods which are known per se (compare J. Chem. Soc. 1969, 211-217- FR-A 2,538,380 (Chem. Abstracts 102 (1985), 61914x); EP-A 180,057; U.S. Pat. No. 4,388,472 and compare Preparation Examples).

Formula (VIII) provides a general definition of the phenol derivatives further required as intermediates. In formula (VIII), Q and m preferably or in particular have those meanings which have already been indicated as preferred or as particularly preferred in connection with the description of the compounds of the formula (I) according to the invention.

Examples of the intermediates of the formula (VIII) which may be mentioned are: 3-methyl-4-trifluoromethyl-phenol, 3-methyl-4-trifluoromethylthio-phenol and 3-methyl-4-trifluoromethylsulphonylphenol.

The compounds of the formula (VIII) are known and/or can be prepared by methods which are known per se (compare EP-A 206,951, DE-A 1,257,784).

In the case in which in formula (VI) m represents zero, the compounds of the formula (VI) are also obtained when phenoxytoluenes of the general formula (IX)

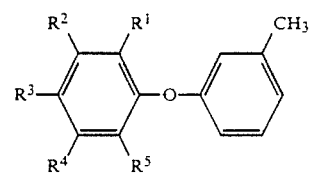
(IX)

in which
R¹, R², R³, R⁴ and R⁵ have the abovementioned meanings, are reacted with hydrogenfluoride/tetrachloromethane at temperatures between 0° C. and 150° C. and pressures between 1 and 50 bar and the product is worked up by customary methods.

Formula (IX) provides a general definition of the phenoxytoluenes to be used as intermediates.

In formula (IX), R¹, R², R³, R⁴ and R⁵ preferably or in particular have those meanings which have already been indicated as preferred or as particularly preferred for R¹, R², R³, R⁴ and R⁵ in connection with the description of the compounds of the formula (I) according to the invention.

Examples of the intermediates of the formula (IX) which may be mentioned are: 3-(2-chloro-4-trifluoromethyl-phenoxy)-toluene, 3-(2,6-dichloro-4-trifluoromethyl-phenoxy)-toluene, 3-(2-chloro-6-fluoro-4-trifluoromethyl-phenoxy)-toluene, 3-(2,3,6-trichloro-4-trifluoromethyl-phenoxy)-toluene, 3-(2,6-dichloro-3-fluoro-4-trifluoromethyl-phenoxy)-toluene and 3-(2,3,6-trifluoro-4-trifluoromethyl-phenoxy)-toluene.

The compounds of the formula (IX) are known and/or can be prepared by processes which are known per se (compare DE-OS (German Published Specification) 2,333,848, DE-OS (German Published Specification) 2,520,815).

In the case in which in formula (VI) m represents 1 and Q represents SO or SO₂, the corresponding compounds of the formula (VI) are also obtained when the compounds of the formula (VI) which can be obtained as described above, in which m represents 1 and Q represents S, are reacted with oxidizing agents, such as, for example, hydrogen peroxide, in the presence of water and if appropriate in the presence of an organic solvent, such as, for example, acetic acid, at temperatures between 0° C. and 100° C. and the product is worked up by customary methods.

Formula (III) provides a general definition of the carbonyl compounds further to be used as starting substances in process (a) according to the invention for the preparation of compounds of the formula (I).

In formula (III), R⁶ and R⁷ preferably or in particular have those meanings which have already been indicated above as preferred or particularly preferred for R⁶ and R⁷ in connection with the description of the compounds of the formula (I) according to the invention.

Examples of the starting substances of the formula (III) which may be mentioned are: malonic acid and also dimethyl malonate, diethyl malonate, dipropyl malonate and dibutyl malonate.

The starting substances of the formula (III) are known chemicals for organic synthesis.

Process (a) according to the invention for the preparation of the new compounds of the formula (I) is preferably carried out using diluents. Suitable diluents here are practically all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylenesulphone and hexamethylphosphoramide, and in addition also alcohols such as methanol, ethanol, propanol, isopropanol, butanol, isobutanol, sec-butanol and tert.-butanol.

Acid acceptors which can be employed in process (a) according to the invention are all acid-binding agents which can customarily be used for reactions of this type. Alkali metal hydroxides such as, for example, sodium hydroxide and potassium hydroxide, alkaline earth metal hydroxides such as, for example, calcium hydroxide, alkali metal carbonates and alkoxides such as sodium carbonate and potassium carbonate, sodium methoxide and potassium methoxide or sodium ethoxide and potassium ethoxide, and in addition aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO) are preferred.

The reaction temperatures can be varied within a relatively large range when carrying out process (a) according to the invention. In general, the reaction is carried out at temperatures between 0° C. and 150° C., preferably at temperatures between 10° C. and 120° C.

Process (a) according to the invention is in general carried out under normal pressure. However, it is also possible to work at elevated or reduced pressure.

For carrying out process (a) according to the invention, the starting substances required in each case are in general employed in approximately equimolar amounts. However, it is also possible to use one of the two components employed in each case in a relatively large excess. The reactions are in general carried out in a suitable diluent in the presence of an acid acceptor, and the reaction mixture is stirred for a number of hours at the temperature required in each case. Working up is in each case carried out by customary methods in process (a) according to the invention.

Formula (I) provides a general definition of the compounds to be used as starting substances in process (b) according to the invention, with the proviso that $R^6$ represents alkoxycarbonyl and $R^7$ represents alkoxy In this case, Q, $R^1$, $R^2$, $R^3$, $R^4$, $R^5$ and m preferably or in particular have those meanings which have already been indicated above as preferred or as particularly preferred for Q, $R^1$, $R^2$, $R^3$, $R^4$, $R^5$ and m in the context of the description of the compounds of the formula (I) according to the invention;

$R^6$ preferably represents $C_1$–$C_4$-alkoxy-carbonyl, in particular $C_1$–$C_3$-alkoxy-carbonyl, and $R^7$ preferably represents $C_1$–$C_4$-alkoxy, in particular $C_1$–$C_3$-alkoxy.

The starting substances of the formula (I) for process (b) described above are new compounds according to the invention; they can be prepared by process (a) according to the invention Process (b) is preferably carried out in the presence of a hydrolysis auxiliary. Those which are suitable are in particular strong acids, such as, for example, hydrochloric acid or sulphuric acid, or alkali metal hydroxides, such as, for example, sodium hydroxide or potassium hydroxide.

Process (b) is carried out in the presence of water and if appropriate in the presence of an organic solvent. Alcohols, such as, for example, methanol or ethanol are preferably employed as organic solvents.

The reaction temperatures can be varied within a relatively large range when carrying out process (b) according to the invention. In general, the reaction is carried out at temperatures between 10° C. and 150° C., preferably at temperatures between 20° C. and 100° C.

Process (b) according to the invention is in general carried out under normal pressure. However, it is also possible to work at elevated or reduced pressure.

For carrying out process (b), between 0.1 and 10 moles, preferably between 0.5 and 5 moles, of hydrolysis auxiliary are in general employed per mole of starting compound of the formula (I). The reaction components are in general added to each other at room temperature and the reaction mixture is stirred, if necessary at elevated temperature, until completion of the reaction. The reaction product which is obtained in crystalline form, if necessary after concentrating, cooling and acidifying, can be isolated by filtering off with suction.

Formula (I) provides a general definition of the compounds to be used as starting substances in process (c) according to the invention, with the proviso that $R^6$ represents carboxyl and $R^7$ represents hydroxyl.

In this case, Q, $R^1$, $R^2$, $R^3$, $R^4$, $R^5$ and m preferably or in particular have those meanings which have already been indicated above as preferred or as particularly preferred for Q, $R^1$, $R^2$, $R^3$, $R^4$, $R^5$ and m in the context of the description of the compounds of the formula (I) according to the invention.

The starting substances of the formula (I) for process (c) described above are new compounds according to the invention; they can be prepared by processes (a) and (b) according to the invention.

Process (c) according to the invention is carried out as a pyrolytic decarboxylation. For this purpose, the starting substances of the formula (I) are heated "in substance" i.e. without further additives, to temperatures between 100° C. and 300° C., preferably between 150° C. and 200° C., until the evolution of gas has subsided.

The products of the decarboxylation are obtained in crystalline form after cooling.

Formula (I) provides a general definition of the compounds to be used as starting substances in process (d) according to the invention, with the proviso that $R^6$ represents hydrogen and $R^7$ represents hydroxyl.

In this case, Q, $R^1$, $R^2$, $R^3$, $R^4$, $R^5$ and m preferably or in particular have those meanings which have already been indicated above as preferred or as particularly preferred for Q, $R^1$, $R^2$, $R^3$, $R^4$, $R^5$ and m in the context of the description of the compounds of the formula (I) according to the invention.

The starting substances of the formula (I) for process (d) described above are new compounds according to the invention; they can be prepared by process (c) according to the invention.

Process (d) is carried out using a halogenating agent. The customary agents for the reaction of carboxylic acids to give carboxylic acid halides can be employed. Examples of these which may be mentioned are phosgene, thionyl chloride, phosphoryl chloride and benzotrichloride. Thionyl chloride is preferably used as halogenating agent.

Process (d) is optionally carried out in the presence of a catalyst. The catalysts customary for the preparation of acid chlorides from acid, such as, for example, pyridine or dimethylformamide, can be used.

Process (d) is optionally carried out in the presence of a diluent. Inert organic solvents from the series comprising the halogenated hydrocarbons, such as, for example, methylene chloride, chloroform, tetrachloromethane or 1,2-dichloroethane are preferred.

The reaction temperatures can be varied within a relatively large range when carrying out process (d) according to the invention. In general, the reaction is carried out at temperatures between 0° C. and 100° C., preferably at temperatures between 10° C. and 90° C.

Process (d) is in general carried out at normal pressure.

For carrying out process (d), between 1 and 100 moles, preferably between 2 and 50 moles, of halogenating agents are in general employed per mole of starting compound of the formula (I). The reaction components are in general added to each other at room temperature and the reaction mixture is stirred, if necessary at elevated temperature, until completion of the reaction. The reaction product remaining after distilling off the liquid component under reduced pressure can be purified by recrystallization, but can also be employed without further purification for subsequent reactions.

Formula (I) provides a general definition of the compounds to be used as starting substances in process (e) according to the invention, with the proviso that $R^6$ represents hydrogen and $R^7$ represents halogen.

In this case, Q, $R^1$, $R^2$, $R^3$, $R^4$, $R^5$ and m preferably or in particular have those meanings which have already been indicated above as preferred or as particularly preferred for Q, $R^1$, $R^2$, $R^3$, $R^4$, $R^5$ and m in the context of the description of the compounds of the formula (I) according to the invention and $R^7$ preferably represents fluorine, chlorine or bromine, in particular chlorine.

The starting substances of the formula (I) for process (e) described above are new compounds according to the invention; they can be prepared by process (d) according to the invention.

In the compounds of the formula (IV) further to be employed as starting substances for process (e), $R^7$ preferably or in particular has that meaning which has already been indicated above as preferred or as particularly preferred for $R^7$ in the context of the description of the compounds of the formula (I) according to the invention, halogen being excluded.

Examples of the starting substances for process (e) which may be mentioned are: methylamine, ethylamine, propylamine, isopropylamine, cyanoamide, dimethylamine, diethylamine, hydroxylamine, O-methylhydroxylamine, hydrazine, methylsulphonylhydrazine, methanol, ethanol, propanol, isopropanol, butanol, isobutanol, sec-butanol, 2-methoxy-ethanol, 2-ethoxy-ethanol, 2-methylthio-ethanol, 2-ethylthioethanol, 2-benzyloxyethanol, 2-benzylthio-ethanol, diethyl and dimethyl hydroxymethanephosphonate, dimethyl and diethyl 1-hydroxy-ethanephosphonate, dimethyl and diethyl 1-hydroxy-1-phenyl-methanephosphonate, 3-hydroxyfuran, furfuryl alcohol, perhydrofurfuryl alcohol, methyl and ethyl lactate and methyl and ethyl glycolate.

These compounds are known chemicals for synthesis.

Process (e) according to the invention is preferably carried out using diluents. Suitable diluents here are practically all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylene sulphone and hexamethylphosphoramide.

Acid acceptors which can be employed in process (e) according to the invention are all acid-binding agents which can customarily be used for reactions of this type. Alkali metal hydroxides such as, for example, sodium hydroxide and potassium hydroxide, alkaline earth metal hydroxides such as, for example, calcium hydroxide, alkali metal carbonates and alkoxides such as sodium carbonate and potassium carbonate, sodium tert-butoxide and potassium tert-butoxide, and further aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO) are preferred.

The reaction temperatures can be varied within a relatively large range when carrying out process (e) according to the invention. In general, the reaction is carried out at temperatures between 0° C. and 100° C., preferably at temperatures between 10° C. and 50° C.

Process (e) according to the invention is in general carried out under normal pressure. However, it is also possible to work out at elevated or reduced pressure.

For carrying out process (e) according to the invention, the starting substances required in each case are in general employed in approximately equimolar amounts. However, it is also possible to use a relatively large excess of one of the two components employed in each case. The reactions are in general carried out in a suitable diluent in the presence of an acid acceptor and the reaction mixture is stirred for a number of hours at the temperature required in each case.

Working up in process (e) according to the invention is in each case carried out by customary methods. For example, the reaction mixture—if appropriate after concentrating—is diluted with water and the desired reaction product is extracted with an organic solvent which is virtually immiscible with water, for example methylene chloride, chloroform, diethyl ether, toluene or xylene. The organic extraction solution is washed with water, dried using a customary drying agent, such as, for example, sodium sulphate, and filtered. After concentrating the filtrate, the compounds of the formula (I)

are obtained as crude products which can be purified in a customary manner, for example by chromatography and/or by recrystallization.

Formula (I) provides a general definition of the compounds to be used as starting substances in process (f) according to the invention, with the proviso that $R^6$ represents hydrogen and $R^7$ represents hydroxyl.

In this case, Q, $R^1$, $R^2$, $R^3$, $R^4$, $R^5$ and m preferably or in particular have those meanings which have already been indicated above as preferred or as particularly preferred for Q, $R^1$, $R^2$, $R^3$, $R^4$, $R^5$ and m in the context of the description of the compounds of the formula (I) according to the invention.

The starting substances of the formula (I) for process (f) described above are new compounds according to the invention; they can be prepared by process (c) according to the invention.

Formula (V) provides a general definition of the alcohols further to be employed as starting substances in process (f). In the formula (V), R preferably represents $C_1$-$C_6$-alkyl, in particular $C_1$-$C_4$-alkyl.

Examples of the starting substances of the formula (V) which may be mentioned are: methanol, ethanol, propanol, isopropanol, butanol, isobutanol, sec-butanol and tert.-butanol. Process (f) is optionally carried out in the presence of a catalyst. Those which are suitable are preferably strong acids, such as, for example, sulphuric acid, methanesulphonic acid or p-toluenesulphonic acid.

The reaction temperatures can be varied within a relatively large range when carrying out process (f) according to the invention. In general, the reaction is carried out at temperatures between 0° C. and 150° C., preferably at temperatures between 20° C. and 100° C.

Process (f) according to the invention is in general carried out under normal pressure. However, it is also possible to work at elevated or reduced pressure.

For carrying out process (f) according to the invention, the alcohol of the formula (V) is preferably employed in so large an excess that it also serves as a diluent. The reaction components are in general mixed at room temperature and then stirred, preferably at elevated temperature, until completion of the reaction. Working up is carried out by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are suitable for selectively combating monocotyledon and dicotyledon weeds in mocotyledon and dicotyledon cultures both in the pre-emergence and the post-emergence methods. The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-2,2-dimethylpropyl)-1,3,5-triazine-2,4-(1H,3H)-dione or N-(2-benzothiazolyl)-N,N,-dimethylurea for combating weeds in cereals; 4-amino-3-methyl-6-phenyl-1,2,4-triazin-(4H)-one for combating weeds in sugar beets, and 4-amino-6(1,1-dimethylethyl)-3-methylthio-1,2,4-triazin-5(4H)-one and for combating weeds in soy beans, in addition 2,4-dichlorophenoxyacetic acid (2,4-D); 4-(2,4-dichlorophenoxy)butyric acid (2,4-DB); 2,4-dichlorophenoxypropionic acid (2,4-DP), 5-(2-chloro-4-trifluoromethyl-phenoxy)-2-nitro-benzoic acid (ACIFLUORFEN); 2-chloro-2,6-diethyl-N-methoxymethylacetanilide (ALACHLOR); 2-chloro-4-ethylamino-6-isopropylamino-1,3,5-triazine (ATRAZINE); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxybenzonitrile (BROMOXYNIL); ethyl 2-{[(4-chloro-6-methoxy-2-pyrimidinyl)-aminocarbonyl]-aminosulphonyl}-benzoate (CHLORIMURON); 2-chloro-N-{[(4-methoxy-6-methyl-1,3,5-triazin-2-yl)-amino]-carbonyl}-benzolsulphonamide (CHLOROSULFURON); N,N-dimethyl-N'-(3-chloro-4-methylphenyl)-urea (CHLORTOLURON); exo-1-methyl-4-(1-methylethyl)-2-(2-methylphenylmethoxy)-7-oxabicyclo-(2,2,1)-heptane (CINMETHYLIN); 3,6-dichloro-2-pyridincarboxylic acid (CLOPYRALIDE); 2-chloro-4-ethylamino-6-(3-cyanopropylamino)-1,3,5-triazine (CYANAZINE);2-[4-(2,4-dichlorophenoxy)-phenoxy]-propionic acid, its methyl or its ethyl ester (DICLOFOP); 2-[(2-chlorophenyl)-methyl]-4,4-dimethylisoxazolidin-3-one (DIMETHAZONE); S-ethyl N,N-din-propyl-thiocarbamate (EPTAME); 4-amino-6-t-butyl-3-ethylthio-1,2,4-triazin-5-(4H)-one (ETHIOZINE);2-{4-[(6-chloro-2-benzoxazolyl)-oxy]-phenoxy}-propionic acid, its methyl or its ethyl ester (FENOXAPROP); 2-[4-(5-trifluoromethyl-2-pyridyloxy)-phenoxy]-propionic acid or its ester (FLUAZIFOP); [(4-amino-3,5-dichloro-6-fluoro-2-pyridinyl)-oxy]-acetic acid or its 1-methylheptyl ester (FLUROXYPYR); 5-(2-chloro-4-trifluoromethylphenoxy)-N-methylsulphonyl-2-nitrobenzamide (FOMESAFEN); N-phosphonomethyl-glycine (GLYPHOSATE); 2-{4-[(3-chloro-5-(trifluoromethyl)-2-pyridinyl)-oxy]-phenoxy}-propanoic acid or its ethyl ester (HALOXYFOP); 3-cyclohexyl-6-dimethylamino-1-methyl-1,3,5-triazine-2,4-dione (HEXAZINONE);-methyl 2-[4,5-dihydro-4-methyl-4-(1-methylethyl)-5-oxo-1H-imidazol-2-yl]-4(5)-methylbenzoate (IMAZAMETHABENZ); 2-(4,5-dihydro-4-methyl-4-isopropyl-5-oxo-1H-imidazol-2-yl)-pyridine-3-carboxylic acid (IMAZAPYR); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-1H)-imidazol-2-yl]-5-ethyl-pyridin-3-carboxylic acid (IMAZETHAPYR); 3,5-diiode-4-hydroxybenzonitril (IOXYNIL); N,N-dimethyl-N'-(4-isopropylphenyl)-urea (ISOPROTURON); (2-ethoxy-1-methyl-2-oxo-ethyl)-5-[2-chloro-4-(trifluoromethyl)phenoxy]-2-nitrobenzoate (LACTOFEN); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)-carbonyl]-amino]-sulphonyl}-benzoic acid or its methyl ester (METSULFURON); 1-(3-trifluoromethylphenyl)-4-methylamino-5-chloro-6-pyridazone (NORFLURAZON); 4-(di-n-propylamino)-3,5-dinitrobenzenesulphonamide (ORYZALIN); 2-chloro-4-trifluoromethylphenyl-3-ethoxy-4-nitro-phenyl ether (OXYFLUORFEN); N-(1-ethylpropyl)-3,4-dimethyl-2,6-dinitroaniline (PENDIMETHALIN); 0-(6-chloro-3-phenyl-pyridazin-4-yl)-S-octyl-thiocarbonate (PYRIDATE);2-[1-(ethoxamino)-butylidene]-5-(2-ethylthiopropyl)-1,3-cyclohexadione (SETHOXYDIM); 2-chloro-4,6-bis-(ethylamino)-1,3,5-triazine (SIMAZINE); 4-ethylamino-2-t-butylamino-6-methylthio-s-triazine (TERBUTRYNE); methyl 3-[[[(4-methoxy-6-methyl-1,3,5-triazin-2-yl)-amino]-carbonyl]-amino]-sulphonyl]-thiophene-2-carboxylate (THIAMETURON); S-(2,3,3-trichloroallyl) N,N-diisopropylthiolcarbamate (TRIALLATE); 2,6-dinitro-4-trifluoromethyl-N,N-dipropylaniline (TRIFLURALIN); ethyl 2-[4-(6-chloro-quinoxalin-2-yl-oxy)-phenoxy]-propionate (QUIZALOFOPETHYL);

Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.005 and 5 kg of active compound per hectare of soil surface, preferably between 0.01 and 3 kg per ha.

The preparation and use of the active compounds according to the invention can be seen from the following examples.

PREPARATION EXAMPLES

Example 1

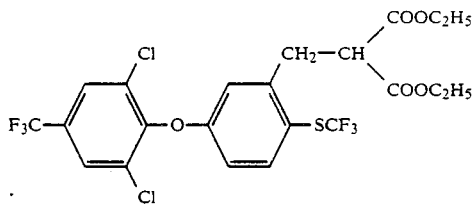

Process (a)

A solution prepared by stirring 4.0 g (0.025 mol) of diethyl malonate, 1.4 g of sodium methoxide and 25 ml of ethanol is evaporated to dryness. 3.7 g (0.020 mol) of the sodium salt of diethyl malonate thus obtained are taken and heated under reflux to boiling together with 8.0 g (0.016 mol) of 2-trifluoromethylthio-5-(2,6-dichloro-4-trifluoromethyl-phenoxy)-benzylbromide and 70 ml of acetonitrile for 20 hours. The mixture is then concentrated, and the residue is stirred with a mixture of silica gel and sodium sulphate and filtered. The filtrate is concentrated, the residue is stirred with a few ml of hexane and the crystalline product is isolated by filtering off with suction.

1.4 g (16 % of theory) of bis-ethyl α-[2-trifluoromethylthio-5-(2,6-dichloro-4-trifluoromethylphenoxy)-benzyl]-malonate of melting point 83° C. are obtained.

EXAMPLE 2

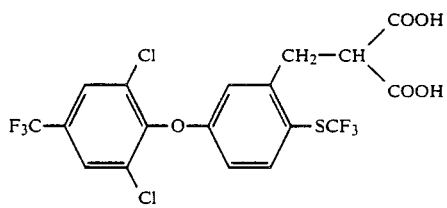

Process (b)

A mixture of 2.6 g (5 mmol) of bis-ethyl α-[2-trifluoromethylthio-5-(2,6-dichloro-4-trifluoromethyl-phenoxy)-benzyl]-malonate, 0.9 g (15 mmol) of potassium hydroxide, 30 ml of ethanol and 20 ml of water is heated to boiling under reflux for 15 hours, then concentrated to about half the volume and acidified with conc. hydrochloric acid. The product, which is obtained crystalline, is isolated by filtering off with suction.

0.4 g (15 % of theory) of α-[2-trifluoromethylthio-5-(2,6-dichloro-4-trifluoromethyl-phenoxy)-benzyl]-malonic acid of melting point 250° C. are obtained.

EXAMPLE 3

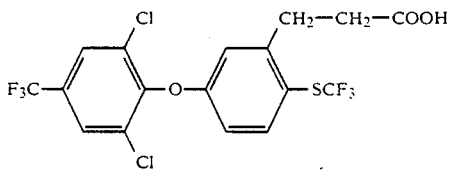

Process (c)

2.7 g (5.2 mmol) of α-[2-trifluoromethylthio-5-(2,6-dichloro-4-trifluoromethyl-phenoxy)-benzyl]-malonic acid are heated to 160° C. to 170° C. for 4 hours. After cooling, 1.6 g (64 % of theory) of β-[2-trifluoromethylthio-5-(2,6-dichloro-4-trifluoromethyl-phenoxy)-phenyl]-propionic acid are obtained as a crystalline residue of melting point 131° C.

EXAMPLE 4

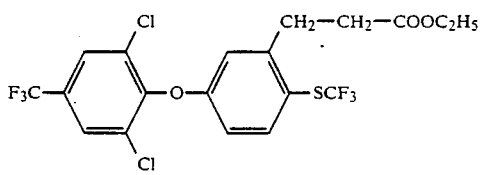

Process (f)

A mixture of 1.0 g (2 mmol) of β-[2-trifluoromethylthio-5-(2,6-dichloro-4-trifluoromethyl-phenoxy)-phenyl]-propionic acid, 80 ml of ethanol and 1 m of conc. sulphuric acid is heated to boiling under reflux for 20 hours and then concentrated. The residue is taken up in chloroform, and this solution is washed with water and with saturated sodium bicarbonate solution, dried using sodium sulphate and filtered. The solvent is carefully removed from the filtrate by distillation in a water jet vacuum.

0.6 g (60 % of theory) of ethyl β-[2-trifluoromethylthio-5-(2,6-dichloro-4-trifluoromethyl-phenoxy)-phenyl]-propionate is obtained as an amorphous residue.

The compounds of the formula (I) shown in Table below can be prepared analogously to Examples 1 to 4 and in accordance with the general description of the preparation process according to the invention.

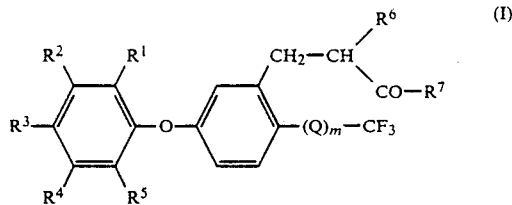

TABLE 4

| | | | Examples of the compounds of the formula (I) | | | | | | |
|---|---|---|---|---|---|---|---|---|---|
| Ex. No. | $R^1$ | $R^2$ | $R^3$ | $R^4$ | $R^5$ | $R^6$ | $R^7$ | Q | m | $^1$H-NMR or melting point/°C. |
| 5 | Cl | H | $CF_3$ | H | Cl | COOH | OH | — | 0 | 138 |

TABLE 4-continued

| | Examples of the compounds of the formula (I) | | | | | | | | | $^1$H-NMR or |
|---|---|---|---|---|---|---|---|---|---|---|
| Ex. No. | $R^1$ | $R^2$ | $R^3$ | $R^4$ | $R^5$ | $R^6$ | $R^7$ | Q | m | melting point/°C. |
| 6 | Cl | H | $CF_3$ | H | Cl | H | OH | — | 0 | 165 |
| 7 | Cl | H | $CF_3$ | H | Cl | H | $OC_2H_5$ | — | 0 | $^1$H-NMR* 1.25/2.60/ 3.10/4.13 |
| 8 | Cl | H | $CF_3$ | H | Cl | H | OH | $SO_2$ | 1 | |
| 9 | Cl | H | $CF_3$ | H | Cl | COOH | OH | $SO_2$ | 1 | 195 |
| 10 | Cl | H | $CF_3$ | H | Cl | $COOC_2H_5$ | $OC_2H_5$ | $SO_2$ | 1 | |
| 11 | Cl | H | $CF_3$ | H | Cl | $COOC_2H_5$ | $OC_2H_5$ | — | 0 | |

*The $^1$H-NMR spectra were recorded in deuterochloroform ($CDCl_3$) using tetramethylsilane (TMS) an internal standard. The chemical shift is given as the δ value in ppm Starting substances of the formula (II)

EXAMPLE (II-1)

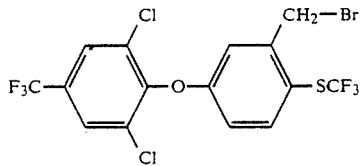

A mixture of 16.5 g (0.04 mol) of 2-trifluoromethylthio-5-[2,6-dichloro-4-trifluoromethyl-phenoxy)toluene, 7.2 g (0.04 mol) of N-bromo-succinimide, 100 ml of tetrachloromethane and a spatula tip full of benzoyl peroxide is heated to boiling under reflux for 48 hours and then filtered. The solvent is carefully removed from the filtrate by distillation in a water jet vacuum.

16.6 g (83 % of theory) of 2-trifluoromethylthio-5-(2,6-dichloro-4-trifluoromethyl-phenoxy)-benzylbromide are obtained as an amorphous residue.

The following are obtained analogously:

EXAMPLE (II-2)

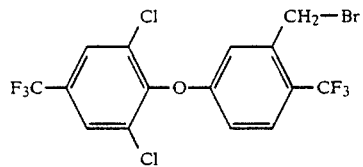

EXAMPLE (II-3)

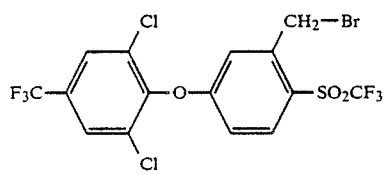

Starting substances of the formula (VI)

EXAMPLE (VI-1)

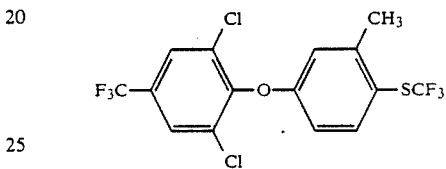

42 g (1.05 mol) of sodium hydroxide powder are added with stirring to a solution of 195 g (0.94 mol) of 3-methyl-4-trifluoromethylthio-phenol in 1.0 l of dimethylformamide, the mixture is then stirred for 30 minutes at 25° C. to 40° C. and diluted with 100 ml of toluene, and then a solvent-water mixture is removed by distillation until an internal temperature of 130° C. is attained. 245 g (1.05 mol) of 3,5-dichloro-4-fluoro-benzotrifluoride are then added and the reaction mixture is stirred for 10 hours at 125° C. The solvent is then substantially removed by distillation at 10 to 20 mbar.

The residue is stirred with a two phase mixture of 300 ml of water and 400 ml of toluene. The organic phase is separated off, dried with sodium sulphate and filtered.

The filtrate is worked up by distillation under reduced pressure. 278 g of crude product of boiling range 125° C. to 133° C. (at 0.1 mbar) are obtained as a main fraction, which gradually crystallizes at 20° C. After pressing dry on clay, 245 g (62 % of theory) of 2-trifluoromethylthio-5-(2,6-dichloro-4-trifluoromethyl-phenoxy)-toluene of melting point 57° C. to 58° C. are obtained.

EXAMPLE (VI-2)

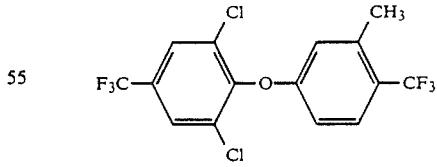

750 ml of hydrogen fluoride (anhydrous) are initially introduced into a VA autoclave at 0° C. to 10° C., and a mixture of 150 g (0.5 mol) of 3-(2,6-dichloro-4-trifluoromethyl-phenoxy)-toluene and 750 ml of tetrachloromethane is added. The mixture is heated to 115° C. under a nitrogen pressure of 3 bar. Hydrogen chloride formed is released at 25 bar through a condenser having an automatic pressure-retaining valve. After 7 hours at 115° C., the mixture is cooled and then excess hydrogen fluoride is recovered by distillation. The residue is washed with water and distilled. 118 g of a product mixture are obtained in a boiling range from 110° C. to 114° C. (0.05 mbar), which contains 67.2 % of 2-trifluoromethyl-5-(2,6-dichloro-4-trifluoromethylphenoxy)-toluene according to gas chromatographic analysis.

EXAMPLE (VI-3)

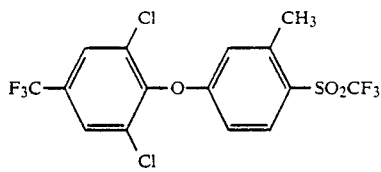

A mixture of 20 g (0.05 mol) of 2-trifluoromethylthio-5-(2,6-dichloro-4-trifluoromethyl-phenoxy)toluene and 100 ml of acetic acid is brought to a temperature between 80° C. and 90° C. and 50 ml of 30 % strength aqueous hydrogen peroxide are added dropwise at this temperature. The reaction mixture is stirred at 100° C. after 3 hours, then cooled to 20° C. and stirred into 250 ml of water.

The product, which is obtained crystalline in this way, is isolated by filtering off with suction.

20 g (93 % of theory) of 2-trifluoromethylsulphonyl-5-(2,6-dichloro-4-trifluoromethyl-phenoxy)toluene of melting point 121° C. to 122° C. are obtained.

USE EXAMPLES

In the following use examples, the compound shown below is used as a comparison substance:

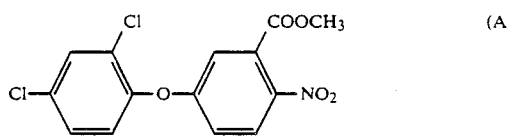

methyl 3-(2,4-dichloro-phenoxy)-6-nitrobenzoate (known from U.S. Pat. No. 3,652,645 and U.S. Pat. No. 3,776,715).

EXAMPLE A

| Pre-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the compound according to Preparation Example 7 shows a very good selective control of monocotyledon and dicotyledon weeds, in particular in monocotyledon cultures such as, for example, wheat.

EXAMPLE B

| Post-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

A clearly superior action, in particular in combating dicotyledon weeds, compared to the comparison substance (A) is shown in this test, for example, by the compound according to Preparation Example 7.

It will be appreciated that the instant specification and claims are set forth by way of illustration and not limitation, and that various modifications and changes may be made without departing from the spirit and scope of the present invention.

What is claimed is:

1. A substituted phenoxyphenylpropionic acid derivative of the formula

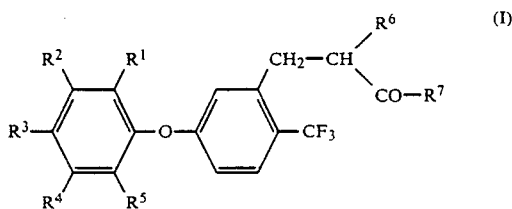

in which
R¹ represents hydrogen, halogen or trifluoromethyl,
R² represents hydrogen or halogen,
R³ represents halogen or trifluoromethyl,
R⁴ represents hydrogen or halogen,
R⁵ represents hydrogen or halogen,
R⁶ represents hydrogen, or alkyl optionally substituted by halogen, and
R⁷ represents halogen, hydroxyl, alkylsulphonylamino, or the grouping O—R⁸, in which
R⁸ represents alkyl, alkenyl, alkynyl or alkoxyalkyl.

2. The compound ethyl β-(2-trifluoromethyl-5-(2,6-dichloro-4-trifluoromethyl-phenoxy)-phenyl-propionate of the formula

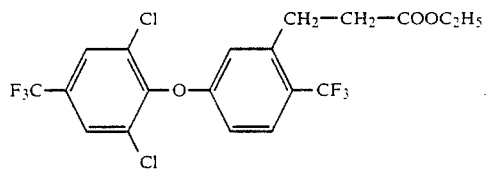

3. A herbicidal composition comprising a herbicidally effective amount of a compound according to claim 1 and a diluent.

4. A method of combating unwanted vegetation which comprises applying to such vegetation or to a locus from which it is desired to exclude such vegetation a herbicidally effective amount of a compound according to claim 1.

5. A method of combating unwanted vegetation which comprises applying to such vegetation or to a locus from which it is desired to exclude such vegetation a herbicidally effective amount of the compound ethyl β-(2-trifluoromethyl-5-(2,6-dichloro-4-trifluoromethyl-phenoxy)phenyl)-propionate of the formula

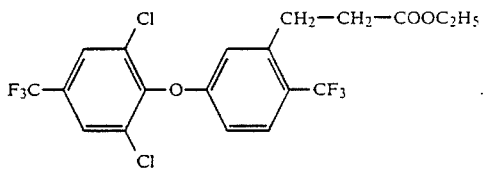

* * * * *